(12) United States Patent
Lovett et al.

(10) Patent No.: US 9,808,557 B2
(45) Date of Patent: Nov. 7, 2017

(54) TUBULAR SILK COMPOSITIONS AND METHODS OF USE THEREOF

(75) Inventors: Michael L. Lovett, Medford, MA (US); Xianyan Wang, Acton, MA (US); Christopher M. Cannizzaro, Washington, DC (US); Gordana Vunjak-Novakovic, New York, NY (US); David L. Kaplan, Concord, MA (US)

(73) Assignees: Trustees of Tufts College, Medford, MA (US); The Trustees of Columbia University in the City of New York, New York, NY (US); Massachussets Institute of Technology, Cambridge, MA (US)

( * ) Notice: Subject to any disclaimer, the term of this patent is extended or adjusted under 35 U.S.C. 154(b) by 1390 days.

(21) Appl. No.: 12/672,521

(22) PCT Filed: Aug. 11, 2008

(86) PCT No.: PCT/US2008/072742
§ 371 (c)(1),
(2), (4) Date: Feb. 2, 2012

(87) PCT Pub. No.: WO2009/023615
PCT Pub. Date: Feb. 19, 2009

(65) Prior Publication Data
US 2012/0123519 A1     May 17, 2012

Related U.S. Application Data

(60) Provisional application No. 60/995,091, filed on Aug. 10, 2007.

(51) Int. Cl.
| | |
|---|---|
| *A61F 2/06* | (2013.01) |
| *A61L 27/36* | (2006.01) |
| *A61L 27/22* | (2006.01) |
| *A61F 2/08* | (2006.01) |
| *A61L 27/26* | (2006.01) |
| *A61F 2/07* | (2013.01) |
| *A61F 2/82* | (2013.01) |

(52) U.S. Cl.
CPC ............. *A61L 27/227* (2013.01); *A61F 2/08* (2013.01); *A61L 27/26* (2013.01); *A61F 2/07* (2013.01); *A61F 2/82* (2013.01); *A61L 27/3604* (2013.01); *D10B 2211/22* (2013.01); *Y10T 428/13* (2015.01)

(58) Field of Classification Search
CPC .................................................. A61L 27/3604
USPC ....................................................... 623/1.13
See application file for complete search history.

(56) References Cited

U.S. PATENT DOCUMENTS

| | | | |
|---|---|---|---|
| 4,806,355 A | 2/1989 | Goosen et al. | |
| 5,015,476 A | 5/1991 | Cochrum et al. | |
| 5,093,489 A | 3/1992 | Diamantoglou | |
| 5,245,012 A | 9/1993 | Lombari et al. | |
| 5,263,992 A | 11/1993 | Guire | |
| 5,270,419 A | 12/1993 | Domb | |
| 5,576,881 A | 11/1996 | Doerr et al. | |
| 5,843,156 A * | 12/1998 | Slepian et al. ................ | 128/898 |
| 5,902,800 A | 5/1999 | Green et al. | |
| 6,127,143 A | 10/2000 | Gunasekaran | |
| 6,245,537 B1 | 6/2001 | Williams et al. | |
| 6,267,776 B1 | 7/2001 | O'Connell | |
| 6,302,848 B1 | 10/2001 | Larson et al. | |
| 6,310,188 B1 | 10/2001 | Mukherjee | |
| 6,325,810 B1 | 12/2001 | Hamilton et al. | |
| 6,337,198 B1 | 1/2002 | Levene et al. | |
| 6,372,244 B1 | 4/2002 | Antanavich et al. | |
| 6,379,960 B1 | 4/2002 | Popoff et al. | |
| 6,395,734 B1 | 5/2002 | Tang et al. | |
| 2002/0028243 A1* | 3/2002 | Masters ........................ | 424/484 |
| 2003/0028239 A1* | 2/2003 | Dong .......................... | 623/1.13 |
| 2003/0100108 A1 | 5/2003 | Altman et al. | |
| 2004/0030377 A1* | 2/2004 | Dubson et al. .............. | 623/1.13 |
| 2004/0199241 A1* | 10/2004 | Gravett ..................... | A61F 2/07 |
| | | | 623/1.13 |
| 2005/0149173 A1* | 7/2005 | Hunter et al. ............... | 623/1.42 |
| 2005/0149175 A1* | 7/2005 | Hunter et al. ............... | 623/1.42 |
| 2005/0154445 A1* | 7/2005 | Hunter et al. ............... | 623/1.13 |

(Continued)

FOREIGN PATENT DOCUMENTS

| | | |
|---|---|---|
| WO | WO-97/08315 A1 | 3/1997 |
| WO | 2004/060424 A | 7/2004 |

(Continued)

OTHER PUBLICATIONS

Altman GH, et al., "Silk-based biomaterials". 2003, Biomaterials, 24, 401-416.
Jin H-J, et al., "Mechanism of silk processing in insects and spiders". 2003, Nature, 424, 1057-1061.
Jin H-J, et al., "Biomaterial Films of Bombyx Mod Silk Fibroin with Poly(ethylene oxide)". 2004, Biomacromolecules, 5, 711-717.
Horan RL, et al., "In vitro degradation of silk fibroin". 2005, Biomaterials, 26, 3385-3393.
Li C, et al., "Electrospun silk-BMP-2 scaffolds for bone tissue engineering". 2006, Biomaterials, 27, 3115-3124.
Sarkar S, et al., "Development and characterization of a porous micro-patterned scaffold for vascular tissue engineering applications". 2006, Biomaterials, 27, 4775-4782.
Sofia S, et al., "Functionalized silk-based biomaterials for bone formation". 2001, J Biomed Mater Res, 54, 139-148.
Wang X, et al., "Biomaterial Coatings by Stepwise Deposition of Silk Fibroin". 2005, Langmuir, 21, 11335-11341.

(Continued)

*Primary Examiner* — Jacqueline Woznicki
(74) *Attorney, Agent, or Firm* — Choate, Hall & Stewart LLP

(57) ABSTRACT

Described are tubular silk fibroin compositions and methods for their manufacture and use. Tubular compositions as described herein can be produced in a range of high burst strengths, can easily be made in a range of inner diameters, can be derivatized with functional moieties, and can be produced in a range of permeabilities suitable for particularized uses. In one aspect, the tubular compositions can be used in the repair or replacement of damaged or diseased blood vessels, including, but not limited to vessels smaller than about 6 mm.

23 Claims, 9 Drawing Sheets

(56) References Cited

U.S. PATENT DOCUMENTS

| | | | |
|---|---|---|---|
| 2005/0154453 A1* | 7/2005 | Hunter et al. | 623/1.42 |
| 2005/0154454 A1* | 7/2005 | Hunter et al. | 623/1.42 |
| 2005/0165467 A1* | 7/2005 | Hunter et al. | 623/1.13 |
| 2006/0073207 A1 | 4/2006 | Masters et al. | |
| 2006/0228389 A1* | 10/2006 | Li et al. | 424/422 |
| 2014/0093580 A1 | 4/2014 | Kaplan et al. | |
| 2014/0288638 A1* | 9/2014 | Knight et al. | 623/1.39 |

FOREIGN PATENT DOCUMENTS

| | | |
|---|---|---|
| WO | 2004/062697 A | 7/2004 |
| WO | 2004/080346 A | 9/2004 |
| WO | WO-2005/012606 A2 | 2/2005 |
| WO | 2005/094911 A | 10/2005 |
| WO | 2006/030182 A | 3/2006 |
| WO | 2007/016524 A | 2/2007 |
| WO | 2007/019439 A | 2/2007 |
| WO | 2007/020449 A | 2/2007 |

OTHER PUBLICATIONS

Wang Y, et al., "In vitro cartilage tissue engineering with 3D porous aqueous-derived silk scaffolds and mesenchymal stem cells". 2005, Biomaterials, 26, 7082-7094.

International Search Report for PCT/US2008/072742, 5 pages (dated Nov. 24, 2008).

Written Opinion for PCT/US2008/072742, 6 pages (dated Nov. 24, 2008).

Baguneid, M.S. et al., Tissue engineering of blood vessels, Br. J. Surg., 93(3):282-90 (2006).

Bosiers, M. et al., Heparin-bonded expanded polytetrafluoroethylene vascular graft for femoropopliteal and femorocrural bypass grafting: 1-year results, J. Vasc. Surg., 43(2):313-8; discussion 318-9 (2000).

Hersel, U. et al., RGD modified polymers: biomaterials for stimulated cell adhesion and beyond, Biomaterials, 24:4385-415 (2003).

Heyligers, J.M. et al., Heparin immobilization reduces thrombogenicity of small-caliber expanded polytetrafluoroethylene grafts, J. Vasc. Surg., 43(3):587-91 (2006).

Isenberg, B.C. et al., Small-diameter artificial arteries engineered in vitro, Circ. Res., 98(1):25-35 (2006).

Kim, U.J. et al., Structure and properties of silk hydrogels, Biomacromolecules, 5(3):786-92 (2004).

L'Heureux, N. et al., A completely biological tissue-engineered human blood vessel, FASEB J., 12(1):47-56 (1998).

Lewus, K.E. et al., In vitro characterization of a bone marrow stem cell-seeded collagen gel composite for soft tissue grafts: effects of fiber number and serum concentration, Tissue Eng., 11(7-8):1015-22 (2005).

Lucas, F. et al., The silk fibroins, Adv. Protein. Chem., 13:107-242 (1958).

Nazarov, R. et al., Porous 3-D scaffolds from regenerated silk fibroin, Biomacromolecules, 5(3):718-26 (2004).

Schaffner, P. and Dard, M.M., Structure and function of RGD peptides involved in bone ; biology, Cell. Mol. Life Sci., 60(1):119-32 (2003).

Soffer, L. et al., Silk-based electrospun tubular scaffolds for tissue-engineered vascular grafts, J. Biomater. Sci. Polym. Ed., 19(5):653-64 (2008).

* cited by examiner

TUBULAR SILK COMPOSITIONS AND METHODS OF USE THEREOF

CROSS REFERENCE TO RELATED APPLICATION

This application is a 35 U.S.C. §371 U.S. National Phase Entry of International Application No. PCT/US2008/072742 filed Aug. 11, 2008, which designates the U.S., and which claims the benefit of priority under 35 U.S.C. §119(e) of U.S. provisional Application No. 60/955,091, filed Aug. 10, 2007, the contents of which are herein incorporated by reference in its entirety.

GOVERNMENT SUPPORT

This invention was made with government support under Grant No. EB002520 awarded by the Tissue Engineering Resource Center (TERC) through the National Institutes of Health from the National Institute of Biomedical Imaging and Bioengineering. The government has certain rights in the invention.

FIELD OF THE INVENTION

The invention relates to tubular compositions comprising silk fibroin. The invention further relates to the repair and replacement of blood vessels.

BACKGROUND OF THE INVENTION

Peripheral arterial disease currently afflicts approximately eight million Americans (Statistical Fact Sheet, 2004, http://www.americanheart.org/presenter.jhtml?identifier=2021), a number expected to rapidly increase as the population ages and becomes more susceptible to cardiovascular disease. Currently, more than 450,000 coronary artery bypass graft procedures are performed each year (Mitchell S L, and Niklason L E, 2003, Cardiovasc Pathol 12(2):59-64). The 'gold standard' of care in these cases is autologous grafting, where a suitable vein or artery from another site of the body (typically a lower limb or the internal mammary artery) is removed and used to bypass the diseased vein or artery. However, in cases where the patient has a particularly complex arterial disease, has previously failed endovascular procedures, or does not have suitable vessels to harvest, synthetic or tissue-engineered vessels can provide an alternative (Baguneid M S, et al., 2006, Br J Surg. 93(3):282-290).

Clinically, two of the more successful synthetic vascular graft materials are expanded polytetrafluoroethylene (ePTFE, Teflon®) and polyethylene terephthalate (PET, Dacron®) (Kannan R Y, et al., 2005, Biomaterials 26(14): 1857-1875). When modified with an anticoagulant such as heparin, or seeded with endothelial cells to generate a tissue-engineered vessel, these synthetic graft materials approach the 'gold standard' of 75% for 5-year patency of autologous vein grafts in human trials (Baguneid M S, et al., 2006, Br J Surg. 93(3):282-290; Meinhart J G, et al., 2001, Ann Thorac Surg. 71(5 Suppl):S327-331; Lambert A W, et al., 1999, Cardiovasc Surg. 7(5):491-494). These results, however, were only achieved for relatively larger diameter grafts (6 to 7 mm inner diameter, ID). When synthetic materials such as unmodified PTFE are used as a microvascular graft for vessels less than 1 mm in diameter, the patency rate drops below this 'gold standard' (Harris J R and Seikaly H, 2002, J Otolaryngol 31(2):89-92). In fact, while heparin-bonded ePTFE macrovascular grafts are commercially available in Europe and have recently been approved by the U.S. Food & Drug Administration (FDA clears GORE PROPATEN vascular graft, 2006 [cited Feb. 19, 2007], http://www.goremedical.com/press/news/propaten-uslaunch2006), no microvascular graft (natural, synthetic, or tissue-engineered) has been fully accepted into routine clinical practice, leaving significant room for improvement in the field (Bosiers M, et al., 2006, J Vasc Surg. 43(2):313-318; discussion 318-319; Heyligers J M, et al., 2006, J Vasc Surg. 43(3):587-591).

Silk coated substrates and the use of silk coatings for the delivery of drugs or other bioactive agents is described in WO 2007/016524.

SUMMARY OF THE INVENTION

The invention provides tubular compositions comprising silk fibroin, methods of making them and methods for their use. Tubular compositions as described herein can be produced in a range of high burst strengths, can easily be made in a range of inner diameters, can be derivatized with functional moieties, and can be produced in a range of permeabilities suitable for particularized uses. In one aspect, the tubular compositions can be used in the repair or replacement of damaged or diseased blood vessels, including, but not limited to vessels smaller than about 6 mm.

In one aspect, the invention provides a tubular composition having a wall defining an inner lumen diameter of less than 6 mm, the tubular composition comprising silk fibroin, wherein said tubular composition has a burst strength of at least 1680 mm Hg. Higher burst strengths for compositions of this aspect and others described herein can be achieved, e.g., at least 2,000 mm Hg, at least 2,200 mm Hg, at least 2,400 mm Hg, at least 2,600 mm Hg, at least 2,800 mm Hg, at least 3,000 mm Hg, at least 3,200 mm Hg, at least 3,400 mm Hg, at least 3,600 mm Hg or higher.

Higher burst strengths can be achieved, for example, by depositing more than one layer of silk fibroin on the rod. Thus, in one embodiment of this aspect and others described herein, tubular compositions can comprise a plurality of layers of silk fibroin, e.g., two layers or more, three layers or more, four layers or more, five layers or more, etc.

In another embodiment of this aspect and others described herein, the wall is not porous.

In another embodiment of this aspect and others described herein, the wall has an apparent permeability coefficient of $8.8 \times 10^{-4}$ cm/s or lower, e.g., $8.5 \times 10^{-4}$ cm/s or lower, $8.0 \times 10^{-4}$ cm/s or lower, $7.0 \times 10^{-4}$ cm/s or lower, $6.0 \times 10^{-4}$ cm/s or lower, $5.5 \times 10^{-4}$ cm/s or lower, $5.0 \times 10^{-4}$ cm/s or lower, $4.0 \times 10^{-4}$ cm/s or lower, $3.0 \times 10^{-4}$ cm/s or lower, $2.0 \times 10^{-4}$ cm/s or lower, $1.0 \times 10^{-4}$ cm/s or lower, $5.0 \times 10^{-5}$ cm/s or lower, $2.5 \times 10^{-5}$ cm/s or lower, $2.0 \times 10^{-5}$ cm/s or lower, $1.5 \times 10^{-5}$ cm/s or lower, $1.3 \times 10^{-5}$ cm/s or lower, $1.2 \times 10^{-5}$ cm/s or lower, or $1.1 \times 10^{-5}$ cm/s or lower, wherein the permeability coefficient is measured according to methods described herein below.

In another embodiment of this aspect and others described herein, the wall is permeable to proteins but prevents the passage of cells through said wall under physiological vascular pressures.

In another embodiment of this aspect and others described herein, the inner lumen diameter is 0.1 mm to 5.9 mm.

In another embodiment of this aspect and others described herein, the silk fibroin is predominantly in a β-sheet conformation.

Tubular compositions of this aspect and others described herein can be implanted in a mammal, including a human. The composition can be implanted in a manner such that it repairs or replaces all or a part of a blood vessel.

In another embodiment of this aspect and others described herein the tubular composition comprises a vascular endothelial cell associated with the inner wall of the tubular composition. The vascular endothelial cell can be associated with the tubular composition before the composition is implanted.

In another embodiment of this aspect and others described herein, the tubular composition can further comprise a bioactive material, e.g., a material including, but not limited to a cell, a peptide, a polypeptide and a therapeutic agent. Bioactive materials can provide, in addition to therapeutic benefits, advantages for the acceptance or integration of the tubes in a subject or other functional advantages. For example, functionalization with peptides, such as RGD peptides or other functional moieties can assist in the attachment of cells, e.g., vascular endothelial cells to one or more surfaces of a tube. Therapeutic agents can be selected, for example, from the group consisting of a protein, a peptide, a nucleic acid, an aptamer, an antibody and a small molecule.

In another aspect, the invention provides a tubular composition having a wall defining an inner lumen diameter of less than 6 mm, the composition comprising silk fibroin and polyethylene oxide.

In one embodiment of this aspect and others described herein, the proportions of silk fibroin and polyethylene oxide are in the range of 99.5/0.5 weight percent to 90/10 weight percent.

In another embodiment of this aspect and others described herein, the tubular synthetic composition has a burst strength of at least 1680 mm Hg.

In another aspect, the invention provides a method of making a tubular composition, the method comprising the steps of: a) providing an aqueous preparation of silk fibroin; b) contacting a rod of a selected diameter with the aqueous preparation of silk fibroin to coat the rod in silk fibroin; c) drying the preparation on the rod; and d) removing the preparation from the rod, whereby a tube or tubular composition comprising silk fibroin is prepared.

In one embodiment of this aspect, steps (b)-(c) are repeated at least once, thereby generating a tubular composition comprising at least two layers of silk fibroin.

In another embodiment, the contacting of step (b) comprises dipping the rod into the aqueous preparation of silk fibroin. Alternatively, the silk fibroin preparation can be sprayed onto the rod.

In another embodiment, the method involves the step, after step (b), of contacting the rod with methanol.

In another embodiment, the drying step comprises drying the preparation in a stream of dehydrating gas, including, but not limited to a stream of nitrogen, $CO_2$, or even hot air.

In another embodiment, the removing of step (d) comprises contacting the preparation on the rod with a surfactant solution.

In another embodiment, the aqueous preparation of silk fibroin comprises polyethylene oxide. The polyethylene oxide can be present at a silk fibroin/PEO ratio in the range of 99.5/0.5 weight percent to 90/10 weight percent.

In another embodiment, the tubular composition has a burst strength of at least 1680 mm Hg or higher.

In another embodiment, the rod is a stainless steel rod. Alternatively, the rod can be made of any material that supports silk fibroin deposition and that permits the release of the silk fibroin tube after the tube is formed on it. Alternative materials include, for example, TEFLON™, polyurethane, other polymers or plastics, and other metals. The rod can have a diameter of, for example 0.1 to 6 mm, which includes any size therebetween.

The functional or structural characteristics of the silk fibroin tubular compositions described herein are readily tailored to provide characteristics suitable for a particular use or situation. For example, where strength is critical, the number of layers of silk fibroin and/or the concentration of silk fibroin in the aqueous preparation can be increased. Sizes can be adjusted at will by changing the diameter of the rod on which the silk layers are deposited. Where the transport of proteins, cells or other agents from the lumen of the tubes to the outside is important, the porosity of the tubes can be adjusted by adjusting an amount of biocompatible polymer, e.g., PEO present in the aqueous preparation of silk fibroin. As will become apparent upon reading the Examples provided herein, the size, strength and porosity of silk fibroin tubes can each be tailored, alone or together, to provide tubes with properties suitable for a wide range of uses.

In another embodiment, the aqueous preparation of silk fibroin comprises a bioactive material that is or becomes associated with the tubular composition. The bioactive material can be, for example, a therapeutic agent. Suitable therapeutic agents can be selected, for example, from a protein, a peptide, a nucleic acid, an aptamer, an antibody and a small molecule.

In another aspect, a method of repairing or replacing all or a part of a blood vessel in a mammal is provided. The method comprises implanting in the mammal a tubular composition comprising silk fibroin as described herein. In one embodiment, the tubular composition has a wall defining an inner lumen diameter of less than 6 mm. In another embodiment, the tubular composition has an inner lumen diameter of 0.1 to 6 mm or any desired size in between. In another embodiment, the tubular composition has a burst strength of at least 1680 mm Hg.

In some aspects, the tubular composition described herein can consist of silk fibroin. In other aspects, the tubular composition can consist essentially of silk fibroin—that is, any other constituents of the tubular composition are not essential to its structural or functional integrity as, for example, a vessel for carrying blood under physiological conditions. A tubular composition as described herein specifically excludes tubular constructs in which a framework or support made of another material is coated with silk. Thus, the compositions of the invention specifically exclude, for example, stents or other structures that carry a coating comprising or consisting of silk on inner or outer surfaces or both. The tubular compositions described herein do not rely upon other materials for either their physical support or their tubular shape. Thus, the tubular compositions described herein are self-supporting. To the extent that such tubes become associated on their inner (lumenal) or outer surfaces with cells or biological matrices, these cells or matrices can provide additional support for the general shape of the tubes, but it should be understood that such cells or matrices are not required to support or maintain the shape of the tubes.

As used herein, the term "porous" refers to the property of a tubular composition described herein to permit the passage of materials through the wall of the tube (in contrast to their passage through or along the lumen of the tube). Tubes described herein encompass a range of porosities, from those that do not substantially permit the passage of cells or proteins, to those that substantially permit the passage of proteins, but not cells, to those that permit the passage of both. As used herein, the term "not porous" means that a tube as described herein does not substantially permit the passage of Alexa-Fluor-488-labeled BSA through the wall of the tube over the course of a 20 minute assay as described herein in Example 5. By "not substantially permit" is meant that under the detection conditions described herein in Example 5, no labeled BSA from inside the tube is detected outside the tube after a 20 minute assay. Alternatively, the porosity of a tubular composition as described herein can be expressed in terms of a permeability coefficient, measured/calculated as described herein. Tubular compositions as described herein are considered "not porous" to the passage of proteins or cells if the permeability coefficient for Alexa-Fluor-488-labeled BSA is $7.3 \times 10^{-4} \pm 1.5 \times 10^{-4}$ cm/s or lower.

As used herein, the term "permeable to proteins" means that a tubular composition as described herein permits the passage of Alexa-Fluor-488-labeled BSA through the tube wall with a permeability coefficient, measured as described herein, of at least $8.9 \times 10^{-4}$ cm/s.

As used herein, the term "burst strength" refers to the pressure, usually expressed in mm Hg, at which a tubular composition, e.g., a synthetic vascular tubular composition as described herein, bursts. To avoid doubt in determining whether a given tubular composition has a burst strength greater than or less than a given value, the burst strength is measured as described in Example 4 herein.

The inner diameter of a tubular composition described herein can vary, for example, from about 0.1 mm to about 6 mm or more, and is preferably less than 6 mm. As described herein, it is very straightforward to prepare synthetic tubular compositions or constructs of specific inner lumen diameters simply by using a rod of the desired diameter in the process of making the tubular silk composition. Specific sizes include, for example, 0.1 mm, 0.2 mm, 0.3 mm, 0.4 mm, 0.5 mm, 0.6 mm, 0.7 mm, 0.8 mm, 0.9 mm, 1.0 mm, 1.2 mm, 1.4 mm, 1.6 mm, 1.8 mm, 2.0 mm, 2.2 mm, 2.4 mm, 2.6 mm, 2.8 mm, 3.0 mm, 3.2 mm, 3.4 mm, 3.6 mm, 3.8 mm, 4.0 mm, 4.2 mm, 4.4 mm, 4.6 mm, 4.8 mm, 5.0 mm, 5.2 mm, 5.4 mm, 5.6 mm, 5.8 mm and 5.9 mm. The preferred sizes can also be expressed as a range, e.g., 0.1 to 5.9 mm, 0.1 to 4 mm, 0.1 to 3 mm, 0.1 to 2 mm, 0.1 to 1 mm, 1.0 to 5 mm, 1.0 to 4 mm, 1.0 to 3 mm, 1.0 to 2 mm, etc.

Concentrations, amounts, sizes, porosities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, an inner diameter range of about 1.0 to about 3.0 mm should be interpreted to include not only the explicitly recited size limits of 1.0 to about 3.0 mm, but also to include individual dimensions such as 1.4 mm, 1.8 mm, 2.0 mm, and 2.7 mm, as well as sub-ranges such as 1.0-1.4 mm, 1.0-1.8 mm, 1.8-2.4 mm, 1.4-3.0 mm, etc. Further, such an interpretation should apply regardless of the breadth of the range or the characteristic being described, such as protein concentration, tubular porosity, lumen diameter, PEO concentration and amounts and concentrations of other ingredients or agents.

As used herein, the term "predominantly in a β-sheet conformation" means that a given polypeptide has at least 60% β-sheet conformation as determined by Fourier-transform infrared spectroscopy (FT-IR). The term includes, for example, at least 60%, at least 65%, at least 70%, at least 75%, at least 80%, at least 85%, at least 90%, at least 95% and even 100% β-sheet conformation.

As used herein, the term "small molecule" refers to any of a class of molecules of less than about 10 kDa molecular weight, including, but are not limited to synthetic organic or inorganic compounds, peptides, (poly)nucleotides, (oligo) saccharides and the like. Small molecules specifically include small non-polymeric (i.e. not peptide or polypeptide) organic and inorganic molecules. Preferred small molecules have molecular weights of less than about 2,000 Da, preferably less than about 1,000 Da, less than about 750 Da, or less than about 500 Da.

DETAILED DESCRIPTION

Figure 1:
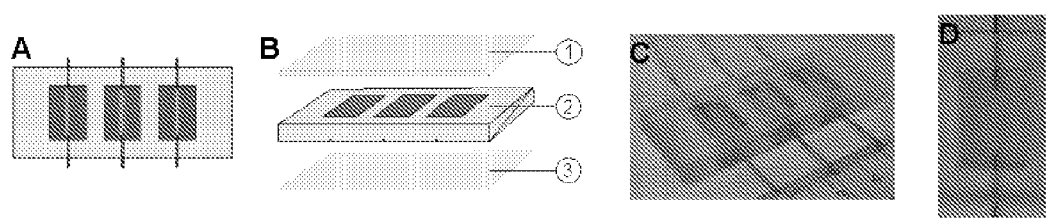
FIG. 1. Bioreactor schematic. (A) Three bioreactors of dimension 10 mm×15 mm×5 mm are arranged within a 25 mm×60 mm×5 mm PDMS block, with 15 mm center-to-center spacing between each bioreactor. Each bioreactor is perfused by 23G stainless steel needles. The needles are spanned by silk microtubes (500 μm inner diameter) and are perfused at a rate of 4 μL/min. The needles are approximately 500 μm from the cover glass to allow for confocal imaging. (B) The devices are assembled from layers of PDMS and glass consisting of a glass slide (1), a bioreactor layer (2), and a glass cover slip (3). The glass cover slip is attached via plasma treatment and the glass slide is attached using label tape. (C) Image of bioreactor. (D) Image of single well with silk tube and collagen gel.

Described herein are silk fibroin microtubes, methods of making them and methods of using them. Among other uses, these tubular compositions can provide small-caliber (<6 mm ID) blood vessel surrogates. Silk fibroin, derived from *Bombyx mori* silkworm cocoons, is well-characterized and widely used in other biomedical applications, particularly as sutures (Altman G H, et al., 2003, Biomaterials 24(3):401-416). This protein is biocompatible, degrades slowly in the body, is readily modified into a variety of formats and generates mechanically robust materials (Altman G H, et al., 2003, Biomaterials 24(3):401-416). These properties, in addition to compliance, variable size, good suture retention, low thrombogenicity, and non-toxicity and -immunogenicity, among others, represent the qualities of an ideal blood vessel substitute (Baguneid M S, et al., 2006, Br J Surg. 93(3):282-290). Processing methods described herein allow for the manufacture of microtubes of varying inner diameter, porosity, mechanical strength, and diffusivity. These properties were experimentally verified via SEM imaging, mechanical testing, enzymatic degradation, and protein diffusion measurements. The biocompatibility and efficacy of the silk microtubes as a microvessel surrogate have been evaluated in vitro by monitoring the perfusion and migration of endothelial cells through the silk microtube and into a surrounding collagen gel. The results indicate that such silk microtubes can be used in the repair or replacement of damaged or diseased blood vessels. The ability to prepare microtubes at least as small as 0.1 mm, in combination with the other advantageous properties noted herein, permits such silk microtubes to be used to repair or replace vessels having an inner lumen of similar or smaller size.

The preparation of silk fibroin solutions has been described previously, e.g., in WO 2007/016524, which is incorporated herein by reference in its entirety. The reference describes not only the preparation of aqueous silk fibroin solutions, but also such solutions in conjunction with bioactive agents.

The silk fibroin solution used in methods and compositions described herein is obtained from a solution containing a dissolved silkworm silk, such as, for example, from *Bombyx mori*. Alternatively, the silk fibroin solution is obtained from a solution containing a dissolved spider silk, such as, for example, from *Nephila ciavipes*. The silk fibroin solution can also be obtained from a solution containing a genetically engineered silk. The genetically engineered silk can, for example, comprise a therapeutic agent, e.g., a fusion protein with a cytokine, an enzyme, or any number of hormones or peptide-based drugs, antimicrobials and related substrates.

The tubular silk compositions described herein, and the methods using them can be performed in the absence of any organic solvent. Thus, these compositions and methods are particularly amenable to the incorporation of labile molecules, such as bioactive agents or therapeutics, and can, in certain embodiments, be used to produce controlled release biomaterials. Preferably, the methods are performed in water only.

As used herein, the term "fibroin" includes silkworm fibroin and insect or spider silk protein (Lucas et al., Adv. Protein Chem 13: 107-242 (1958)). Preferably, fibroin is obtained from a solution containing a dissolved silkworm silk or spider silk. The silkworm silk protein is obtained, for example, from *Bombyx mori*, and the spider silk is obtained from *Nephila clavzes*. In the alternative, the silk proteins suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

The silk fibroin solution can be prepared by any conventional method known to one skilled in the art. Preferably the solution is an aqueous solution. For example, *B. mori* cocoons are boiled for about 30 minutes in an aqueous solution. Preferably, the aqueous solution is about 0.02M $Na_2CO_3$. The cocoons are rinsed, for example, with water to extract the sericin proteins and the extracted silk is dissolved in an aqueous salt solution. Salts useful for this purpose include lithium bromide, lithium thiocyanate, calcium nitrate or other chemicals capable of solubilizing silk. Preferably, the extracted silk is dissolved in about 9-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin. Preferably, the PEG is of a molecular weight of 8,000-10,000 g/mol and has a concentration of 25-50%. A slide-a-lyzer dialysis cassette (Pierce, MW CO 3500) is preferably used. However, any dialysis system can be used. The dialysis is for a time period sufficient to result in a final concentration of aqueous silk solution between 10-30%. In most cases dialysis for 2-12 hours is sufficient.

Alternatively, the silk fibroin solution can be produced using organic solvents. Such methods have been described, for example, in Li, M., et al., J. Appl. Poly Sci. 2001, 79, 2192-2199; Mm, s., et al. Sen I Gakkaishi 1997, 54, 85-92; Nazarov, R. et al., Biomacromolecules 2004 May-June; 5(3):71 8-26.

Concentrated aqueous silk fibroin solutions and methods for preparing the same are described in PCT application PCT/USO4/11199.

In methods and compositions described herein, the deposited aqueous silk fibroin layers can be dehydrated using a stream or gentle flow of dehydrating gas. Any gas with dehydrating properties can be used to dehydrate the aqueous silk fibroin layers between applications to the rod, for example, $CO_2$, $N_2$ or hot air. In addition, means for dehydrating gases are known to those skilled in the art.

In one preferred embodiment, the dehydrating gas is $N_2$. Preferably the dehydrating gas induces a β-sheet structure of fibroin. The layers can be dehydrated to various degrees by changing the amount of time each layer is exposed to the stream of gas.

As used herein the term "dehydrating" refers to the removal of any amount of water, for example, 5-15%, 15-35%, 35-50%, 50%-75%, 75-90%, or 90%-100% removal of water.

In methods and compositions described herein, different bioactive materials or components (e.g. biocompatible polymers) can be entrapped or immobilized in different layers, or in different locations, to facilitate function and utility of the coating. Additionally, layers may be applied that contain no bioactive or therapeutic agents. Such "empty" layers, sometimes referenced to as "barrier layers", are useful in controlling release of the loaded agents. In certain embodiments it may be desirable to coat the rod with an "empty" layer of silk fibroin before coating with a "loaded" layer.

In one embodiment, the tubular silk fibroin composition comprises a therapeutic agent. The silk fibroin solution can be contacted with a therapeutic agent prior to forming the dehydrated fibroin layer on the rod, or can be loaded onto the dehydrated layer after it is formed. In one preferred embodiment, the therapeutic agent is entrapped in the silk upon drying of the aqueous fibroin layer with a stream of gas, e.g., dehydrating the silk fibroin layers with $N_2$ gas induces a conformation change of the fibroin to the beta sheet structure, which entraps the agent. Additional layers can then be added either with the same agent, a different agent or no agent. This stepwise deposition approach also allows entrapment of varied concentrations of therapeutics within each layer.

The variety of different therapeutic agents that can be used in conjunction with the biomaterials of the present invention is vast and includes small molecules, proteins, peptides and nucleic acids. In general, therapeutic agents which can be associated with tubular compositions described herein include, without limitation: anti-infectives such as antibiotics and antiviral agents; viral vectors, chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); nerve growth factors, anti-angiogenic proteins such as endostatin, and other naturally derived or genetically engineered proteins, polysaccharides, glycoproteins, or lipoproteins.

Thus, in addition to their function in the repair or replacement of blood vessels of various sizes, the tubular silk compositions described herein can be used to deliver any type of molecular compound, such as pharmacological materials, vitamins, sedatives, steroids, hypnotics, antibiotics, chemotherapeutic agents, prostaglandins, metals, pigments or dyes, and radiopharmaceuticals. The system is suitable for the delivery of the above materials and others including but not limited to proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

Silk biomaterials containing pharmacological agents may be formulated by mixing one or more therapeutic agents with the aqueous solution that is used to make the tubular silk composition. Alternatively, a therapeutic agent can be loaded onto a pre-formed tubular silk composition, preferably with a pharmaceutically acceptable carrier. Any pharmaceutical carrier can be used that does not dissolve the silk material. The therapeutic agents can be present as a liquid, a finely divided solid, or any other appropriate physical form.

In one embodiment, the tubular silk fibroin composition comprises biologically active compounds that are not therapeutics. For example, compounds that functionalize the composition, such as to render the composition resistant to bacteria (an anti-bacterial coating), or that function in attachment, for example that aid in attachment of cells to the composition. Examples of biologically active compounds include, but are not limited to: cell attachment mediators, such as collagen, elastin, fibronectin, vitronectin, laininin, proteoglycans, or peptides containing known integrin binding domains e.g. "RGD" integrin binding sequence, or variations thereof, that are known to affect cellular attachment (Schaffner P & Dard, 2003, Cell Mol Life Sd. January; 60(1):1 19-32; Hersel U. et al. 2003 Biomaterials November; 24(24):4385-415); biologically active ligands; and substances that enhance or exclude particular varieties of cellular or tissue ingrowth.

Thus, the bioactive agents suitable for use in compositions and methods described herein include any substance capable of exerting a therapeutic or prophylactic effect as well as agents that have positive pharmacological effects on the expression of the extracellular matrix. The bioactive agent can also be for enhancing wound healing (e.g. at a vascular site, particularly a vascular site being repaired with a tubular silk fibroin composition as described herein). Examples of such active ingredients include antiproliferative substances as well as antineoplastic, antiinflammatory, antiplatelet, anticoagulant, antifibrin, antithrombin, antimitotic, antibiotic, antioxidant, and combinations thereof. A suitable example of an antiproliferative substance includes actinomycin D, or derivatives and analogs thereof (manufactured by Sigma-Aldrich 1001 West Saint Paul Avenue, Milwaukee, Wis. 53233; or COSMEGEN available from Merck). Examples of suitable antineoplastics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack-12-N.J.), mitomycin (e.g. Mutamycin® from Bristol-Myers Squibb Co., Stamford, Conn.) and docetaxel. Examples of suitable antiplatelets, anticoagulants, antifibrins, and antithrombins include heparin, sodium heparin, low molecular weight heparin, heparin sulfate, heparin having a hydrophobic counterion, hirudin, argatroban, forskolin, vapiprost, prostacyclin and prostacyclin analogs, dextran, D-phe-pro-arg-chloromethylketone (synthetic antithrombin), dipyridamole, glycoprotein Jib/lila platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinbiastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffluan-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glaxo), Seramin (a PDGF antagonist), serotonin blockers, steroids, thioprotease inhibitors, triazolopyrimidine (a PDGF antagonist), and nitric oxide. Other therapeutic substances or agents which may be appropriate include mannose-6-phosphate, superoxide dismutase, retinoic acid, suramin, asiaticoside, hyaluronan, alpha-interferon, genetically engineered epithelial cells, dexamethasone and rapamycin and structural derivatives or functional analogs thereof, such as 40-O-(2-hydroxy)ethyl-rapamycin (known by the trade name of EVEROLIMUS available from Novartis), 40-O-(3-hydroxy) propyl-rapamycin, 40-O-2-(2-hydroxy)ethoxy ethyl-rapamycin, and 40-O-tetrazole-rapamycin. Exposure of the fibroin solution the active ingredient is not permitted to adversely alter the active ingredient's composition or characteristic. Accordingly, the particular bioactive agent is selected for mutual compatibility with the blended composition.

The dosage or concentration of the bioactive agent required to produce a favorable therapeutic effect should be less than the level at which the active ingredient produces toxic effects and greater than the level at which non-therapeutic results are obtained. For example, the dosage or concentration of the active ingredient required to inhibit the desired cellular activity can depend upon factors such as the particular circumstances of the patient; the nature of the trauma; the nature of the therapy desired; the time over which the ingredient administered resides at the site of treatment; and if other bioactive substances are employed, the nature and type of the substance or combination of substances. Therapeutic effective dosages can be determined empirically, for example, in the case of a vascular graft, by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Biocompatible polymers can also be added to the silk solution to generate composite matrices in the tubular compositions described herein. Biocompatible polymers useful in the compositions described herein include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). Two or more biocompatible polymers can be used.

It is noted that the silk fibroin tubular compositions tend to be clear, rather than opaque. Silk fibroin tubes comprising just silk fibroin, i.e., lacking a biocompatible polymer such as PEO tend to be quite clear to translucent, becoming more opaque by degrees as polymer concentration is increased. The good light transmission properties of the tubes provide an advantage, particularly where, for example, imaging is to be performed. As used herein in this context, the term "clear" means that a tube substantially transmits, rather than absorbs, light in the visible spectrum, particularly when wet with an aqueous medium such as saline, serum or plasma.

In one embodiment, the concentration of salt is increased to favor deposition of silk fibroin onto the rod or onto previous layers of silk. Salt concentration can be increased by addition of any salt to the aqueous silk fibroin solution including, but not limited to, monovalent and divalent salts such as NaCl, KCl and $CaCl_2$. Preferred salts are monovalent, such as NaCl and KCl. In one preferred embodiment, the salt concentration is adjusted using NaCl.

The thickness of each deposited layer can also be controlled by adjusting the concentration of fibroin in the silk fibroin solution used to form the layer. The more concentrated the fibroin in the aqueous silk fibroin solution is, the more fibroin that is deposited on the rod or on the previous layer of silk fibroin and a more compact structure is formed.

Adjusting the pH of the aqueous silk fibroin solution also affects the amount of fibroin deposited on the rod or on the previous layer of silk fibroin on the rod. Although stainless steel is preferred, rods for the deposition of silk fibroin compositions can be made of any of a number of materials, e.g., various polymers or plastics that are insoluble under the conditions chosen for the application of silk compositions. When the rod is a negatively charged material, lowering the pH of the silk fibroin solution favors deposition of the silk fibroin onto the rod. When the rod is a positively charged material, increasing the pH of the silk fibroin solution favors deposition of the silk fibroin onto the material. At a low pH (e.g. 2.0) the silk fibroin chains have a net positive charge, which favors deposition on a negative substrate. In contrast, at a high pH (e.g. 12.5) the silk fibroin chains have a net negative charge, and thus, deposition on a negatively charged substrate is not favored.

All biomaterials as described herein may be sterilized using conventional sterilization process such as radiation based sterilization (i.e. gamma-ray), chemical based sterilization. Preferably the sterilization process will be with ethylene oxide at a temperature between 52-55° C. for a time of 8 hours or less. After sterilization the biomaterials may be packaged in an appropriate sterilized moisture resistant package for shipment.

Tubular compositions described herein can be implanted into a subject in need thereof by one of skill in the art using essentially standard vascular graft approaches. Obviously, the tubes themselves, being made essentially of silk, will support sutures, which themselves are most often made of silk. The size of a graft necessary for a given situation can be selected by the skilled surgeon.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

The invention will be further characterized by the following non-limiting examples which are intended to be exemplary of the invention.

EXAMPLES

Example 1: Preparation of Silk Microtubes

Preparation of Aqueous Silk Fibroin Solutions

A 6-8% (w/v) silk fibroin aqueous solution was obtained from *Bombyx mori* silkworm cocoons using previously described procedures (Kim U J, et al., 2004, Biomacromolecules 5(3):786-792; Li C, et al., 2006, Biomaterials 27(16): 3115-3124). Briefly, the silkworm cocoons (supplied by Tajima Shoji Co., LTD., Yokohama, Japan) were extracted in 0.02 M sodium carbonate solution, rinsed in distilled water, dissolved in 9.3 M lithium bromide, and dialyzed against distilled water using a Slide-a-Lyzer dialysis cassette (molecular weight cutoff MWCO, 3,500, Pierce, Rockford, Ill.) for 48 hours. The resulting 6-8% (w/v) fibroin solution was then concentrated by dialyzing against 10 wt % poly(ethylene glycol) (PEG) to produce a 20-30% (w/v) silk fibroin aqueous solution. All silk fibroin solutions were stored at 4° C. until used to make silk microtubes.

Preparation of Silk Microtubes

Silk microtubes were prepared by dipping stainless steel wire (0.025" (0.64 mm) diameter, Type 304V, Small Parts, Miami Lakes, Fla.) into 20-30% (w/v) silk fibroin. When the stainless steel rods were evenly coated with concentrated silk fibroin, they were then dipped into methanol, inducing a transformation in the concentrated silk fibroin from an amorphous liquid to the β-form silk fibroin conformation, characterized by anti-parallel β-sheets (Jin H J, and Kaplan D L, 2003, Nature 28; 424(6952):1057-1061). The process of alternate dipping in concentrated aqueous silk fibroin solution and methanol was carried out until the stainless steel wire was evenly coated (2-4 times). The silk-coated wire was then left to dry overnight before being cut at each end and placed in a surfactant solution to remove the silk microtube from the steel wire. Silk tubes of differing size were made according to the same procedure by simply by using larger or smaller stainless steel wire or rod.

Example 2. Preparation of Porous Silk Microtubes

Concentrated silk fibroin solutions were blended with varying volumes of 6 wt % poly(ethylene oxide) (PEO) as described previously (Jin H J, et al., 2004, Biomacromolecules May-June; 5(3):711-717) to form blend ratios of silk fibroin/PEO of 100/0, 99/1, 98/2, 90/10, and 80/20 (wt %). The silk fibroin/PEO blends were gently mixed at room temperature using a spatula before sonication for 10 minutes. Silk/PEO microtubes were made using the same dipping technique and dried overnight as described above. After drying, silk/PEO tubes were immersed in distilled water for 24 hours at room temperature, facilitating the extraction of the PEO phase from the silk/PEO microtube, leaving a porous silk microtube.

Silk tubes were manufactured using layer-by-layer deposition of concentrated silk fibroin on a stainless steel rod of defined diameters, using methanol to induce β-sheet formation to provide stability in aqueous solution and improved mechanical properties (Jin H J, and Kaplan D L, 2003, Nature 28; 424(6952):1057-1061). This technique provided solid silk tubes of low pore size distribution and low porosity, restricting nutrient and oxygen diffusion through the walls of the microtubes. To improve these diffusion properties, porous, three-dimensional silk tubes were generated by adding various fractions of PEO to the concentrated silk fibroin (as described in the materials section). By varying the specific weight percent of PEO, defined pore sizes were obtained, with greater weight percentages of PEO creating tubes with larger pore sizes. This provides a measure of control over the microtube permeability.

Silk microtubes were analyzed for surface pore size distribution and roughness at the exterior surface as well as the cross-section of the microtube using SEM. Silk microtube samples were sputter coated with gold using a Polaron SC502 Sputter Coater (Fisons, VG Microtech, East Sussex, England) and imaged using a JEOL JSM-840 Scanning Microscope (JEOL Ltd., Tokyo, Japan). The SEM images, along with image analysis software (ImageJ, National Institutes of Health, USA) were used to determine the mean pore size of the silk microtubes. Fluorescence images of the silk microtubes within the bioreactor were acquired using a Leica DMIRE2 confocal microscope with a TCS SP2 scanner (Leica Microsystems, Mannheim/Wetzlar, Germany).

Figure 2:
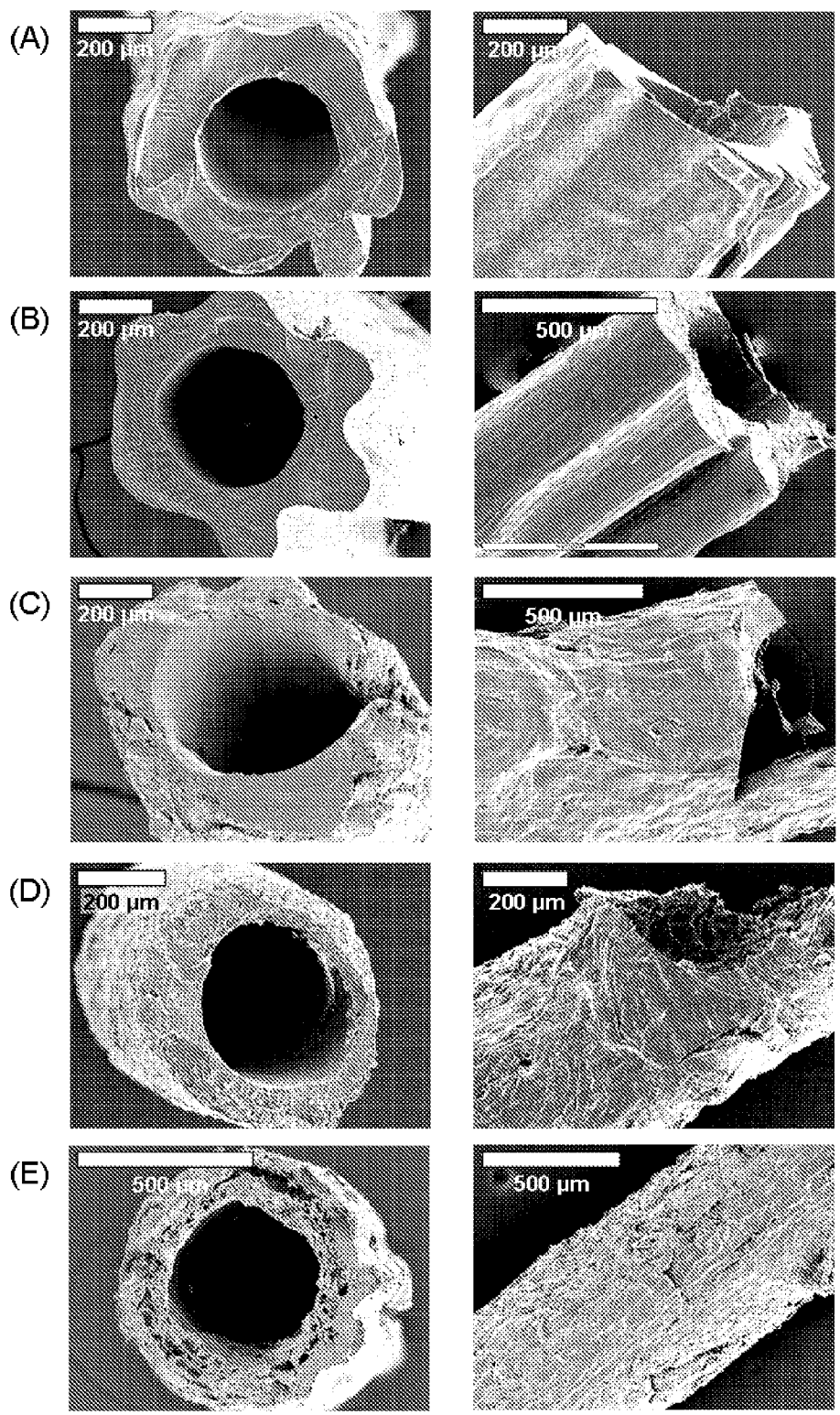
FIG. 2. SEM images of microtubes of silk fibroin and silk fibroin/PEO blends: (A) silk fibroin, (B) 99/1 wt %, (C) 98/2 wt %, (D) 90/10 wt %, (E) 80/20 wt % (silk fibroin/PEO).
Figure 3:
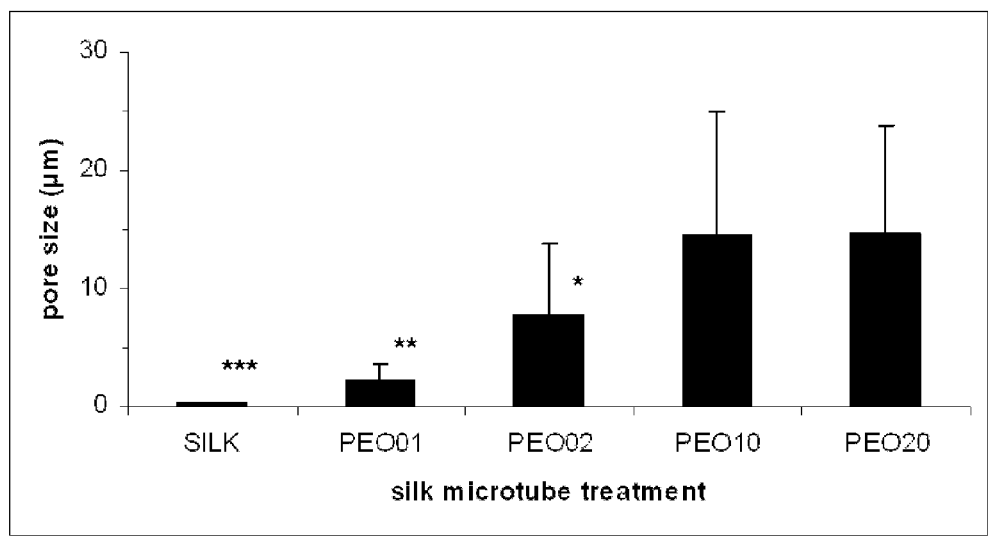
FIG. 3. Pore sizes (μm) of silk fibroin/PEO blend microtubes as a function of microtube treatment. Surface pore sizes of the silk microtubes of different silk fibroin/PEO blends were measured and quantified both along the tube surface and cross-section using SEM images and ImageJ software. Microtube treatments are given either as 100% silk fibroin (SILK) or according to wt % of PEO in a silk fibroin/PEO blend (e.g. PEO01 represents a 99/1 wt % silk fibroin/PEO blend). * indicates P<0.01 with PEO10, PEO20;  indicates P<0.01 with PEO02, PEO10, PEO20; * indicates P<0.01 with PEO01, PEO02, PEO10, PEO20 (two-sample t-test).

As shown in FIG. 2, pore size distributions in the silk microtubes can be controlled by using different weight percentages of PEO. These pore sizes range from the smooth, uniform surface of the 100% silk fibroin microtubes to the rough, highly-porous microtubes composed of the 90/10 wt % silk/PEO or 80/20 wt % silk/PEO blends. Intermediate porosities were achieved using lower weight percentages of PEO (FIG. 2*b,c*). Surface pore size distribution increased as the weight percentage of PEO increased (FIG. 3), which agrees with previously reported results for 2-D films generated from silk/PEO blends (Jin H J, et al., 2004, Biomacromolecules May-June; 5(3):711-717). For the 3-D microtubes, despite similar mean pore size distribution values for 10 and 20 wt % PEO, large void spaces were more prevalent at the higher PEO concentration. As reported below, this increased void fraction likely accounts for decreased mechanical robustness and burst strength of 80/20 wt % silk/PEO blends. This ability to alter microtube pore size distribution creates opportunities to tailor microtube manufacture to specific applications, e.g. high porosity tubes for applications where high transport rates, but not mechanical strength, are needed, versus low porosity tubes where mechanical integrity, but not transport, is critical.

Figure 4:
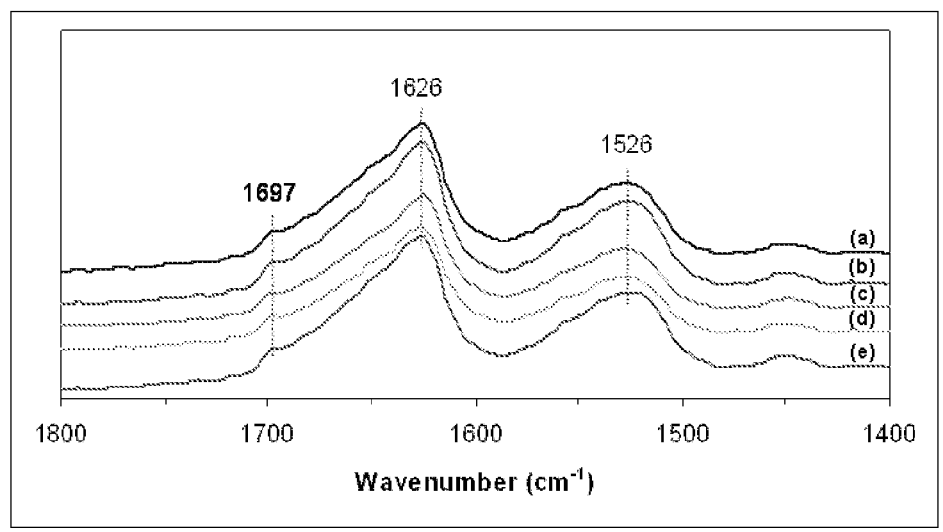
FIG. 4. FT-IR spectra of microtubes of silk fibroin and silk fibroin/PEO blends: (a) silk fibroin, (b) 99/1 wt %, (c) 98/2 wt %, (d) 90/10 wt %, (e) 80/20 wt % (silk fibroin/PEO).

Example 3. Characterization of Silk Fibroin and Silk Fibroin/PEO Microtubes by FT-IR Spectroscopy The presence of β-sheets in all formulations of silk fibroin and silk fibroin/PEO microtubes was confirmed using FT-IR (FIG. 4). The infrared spectra of the silk fibroin and silk fibroin/PEO microtubes were measured using a Bruker Equinox 55/S FT-IR spectrometer. Samples were taken using hydrated microtubes, with each spectrum acquired over the range of 4000-400 $cm^{-1}$ for 66 scans with a resolution of 4 $cm^{-1}$. Each microtube demonstrated a predominantly β-sheet structure (1697 cm-1, 1626 cm-1, amide I; 1526 cm-1, amide II), which was induced by the methanol treatment applied to all microtubes. There were no differences in the amide I and amide II spectral bands between microtubes of pure silk fibroin and those of silk/PEO blends, agreeing with previously reported structural data using silk fibroin and PEO films (Jin H J, et al., 2004, Biomacromolecules May-June; 5(3):711-717).

Example 4. Characterization of Silk Fibroin and Silk Fibroin/PEO Microtubes—Mechanical Strength The burst strengths of the silk microtubes were measured by cannulating the hydrated silk tubes, cut to approximately 1 cm lengths, and filling the tubes at a rate of 0.4 mL/min with water. Silk microtubes were submerged in water during perfusion. Pressure inside the tube was increased by blocking flow out of one end of the tube and recorded using a digital manometer (Sper Scientific, Scottsdale, Ariz.) until tube failure, with the observed maximum pressure logged.

Figure 5:
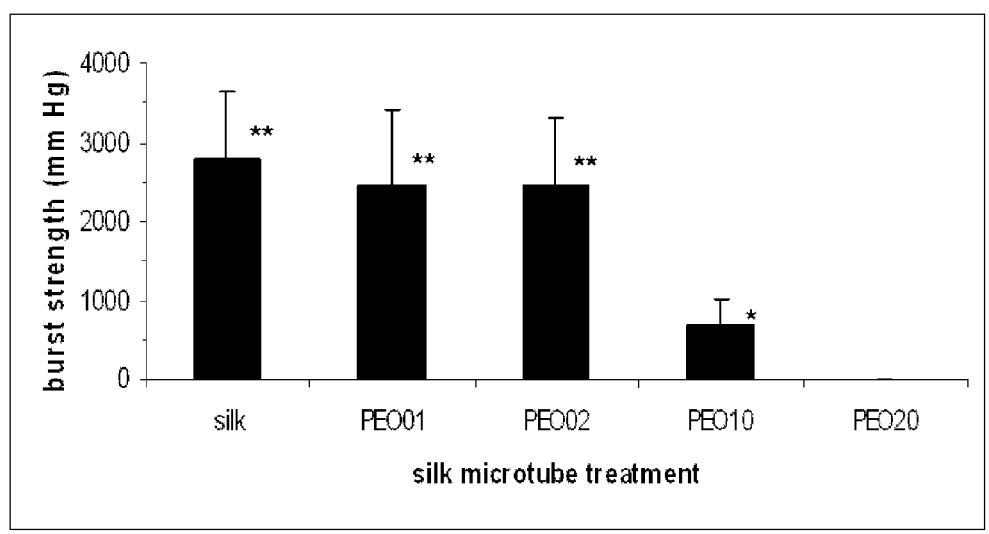
FIG. 5. Burst pressure of silk microtubes as a function of microtube treatment. Internal pressure of the microtubes was increased by flowing water through the microtube, keeping one end of the flow loop closed. Pressure at point of failure was recorded with a digital manometer (n=5-6). * indicates P<0.05 with PEO20; ** indicates P<0.01 with PEO10, PEO20 (two-sample t-test).

The burst pressure of the silk microtubes was a function of pore size distribution, with silk microtubes with smaller pore sizes (100/0, 99/1, and 98/2 wt % silk fibroin/PEO) demonstrating higher burst pressures than those with larger pores (90/10 and 80/20 wt % silk fibroin/PEO) (FIG. 5). Burst pressures for the microtubes of lower porosities were very high, with average burst pressure values of 2780±876 mm Hg, 2470±937 mm Hg, and 2460±844 mm Hg for 100/0, 99/1, and 98/2 wt % silk fibroin/PEO, respectively. While these burst pressures are from smaller caliber vessels, it is worth noting that these burst strengths are significantly higher than those of human saphenous veins (1680±307 mm Hg), the current gold standard for bypass grafts (L'Heureux N, et al., 1998, Faseb J 12(1):47-56), and are also higher than reported burst strengths for electrospun silk tubes (811±77.2 mm Hg) (Soffer L, et al., J Biomater Sci Submitted). Burst strengths of 90/10 and 80/20 wt % silk fibroin/PEO tubes were significantly lower than those values for the tubes with the smaller pore sizes, with values of 680±327 mm Hg and 10±2 mm Hg, respectively. Compared to physiological pressures of approximately 100-140 mm Hg (coronary artery during systole) or 15-40 mm Hg (capillary blood pressure) (Isenberg B C, et al., 2006, Circ Res 6; 98(1):25-35; Williams S A, et al., 1988, Clin Sci (Lond) 74(5):507-512), most microtubes failed above this level, indicating feasibility for future in vivo studies involving tubes manufactured with greater than (or equal to) 90/10 wt % silk fibroin/PEO blends. Microtubes typically failed by developing a leak at one end of the microtube, though occasionally failed by developing a pinhole leak. As indicated by their burst pressures, the low pore size tubes were mechanically robust when compared to the microtubes with larger pore sizes, which were often weak and difficult to cannulate without splitting the tube.

Example 5. Characterization of Silk Fibroin and Silk Fibroin/PEO Microtubes—Protein Permeability Bioreactor Design In order to assess the performance of silk microtubes in terms of protein permeability and endothelial cell biocompatibility, a simple bioreactor system was developed with the capability to culture and image three microtubes (FIG. 1). The bioreactor consisted of a glass cover slip (Goldseal, No. 1, 24×60 mm, Ted Pella, Redding, Calif.) irreversibly bonded using vacuum gas plasma to a PDMS (Sylgard 184, Ellsworth Adhesives, Germantown, Wash.) casting, forming three independent medium wells. The mold for the PDMS casting was machined from a polycarbonate block using a small CNC mill (MDX-15, Roland ASD, Lake Forest, Calif.). The overall dimensions of the PDMS casting were 6.0 cm×2.5 cm×1.0 cm, with 3 wells of dimension 1.0 cm×1.5 cm each. In the center of each well, a stainless steel rod (0.025" diameter, Type 304V, Small Parts, Miami Lakes, Fla.) was positioned approximately 500 µm from the bottom edge of the bioreactor and embedded in the PDMS during the pouring and curing process. This rod served as a space holder for hypodermic, stainless steel needles (23-gauge, BD, Franklin Lakes, N.J.) that were later used to perfuse the microtubes. Pharmed tubing (0.51 mm inner diameter, Cole-Parmer, Vernon Hills, Ill.) was used to perfuse the bioreactor using a syringe pump (Harvard Apparatus, Holliston, Mass.). Microtubes were embedded in a collagen gel matrix in order to mimic in vivo implantation conditions and to allow comparison with previously reported studies on the formation of microvascular tubes (Chrobak K M, et al., 2006, Microvasc Res May; 71(3):185-196).

Preparation of Collagen Gels

Collagen gels were prepared based on a previously developed method (Lewus K E, and Nauman E A, 2005, Tissue Eng 11(7-8):1015-1022) with minor changes. Collagen gels were prepared on ice by mixing 1.22 mL type I rat tail liquid collagen (~4 mg/mL in 0.02 N acetic acid, Upstate Cell Signaling Solutions, Lake Placid, N.Y.), 12.2 µL 2M sodium hydroxide, 20 µL, 100 mM ascorbic acid, and 768 µL of growth medium (Wang Y, et al., 2005, Biomaterials 26(34): 7082-7094) for a final collagen concentration of approximately 2.5 mg/mL. This collagen suspension was then aliquoted in 400 µL volumes into each well of the bioreactor and maintained at 25° C. for 15-30 minutes to allow for even gelation before being placed in the incubator. For long-term experiments, 200 µL of growth medium was added to the top of each gel after 1-2 hours.

Protein Permeability

Protein diffusion through the silk microtubes was assessed by perfusing the silk microtubes embedded within an acellular collagen gel in the bioreactor system with a solution of Alexa-Fluor-488-labeled BSA (50 µg/mL in media, Molecular Probes, Eugene, Oreg.). Fluorescence images were acquired every minute for 20 minutes using confocal microscopy and the apparent permeability coefficient was calculated according to previously described techniques (Chrobak K M, et al., 2006, Microvasc Res May; 71(3): 185-196; Huxley V H, et al., 1987, Am J Physiol 252(1 Pt 2):H188-197). Briefly, the permeability coefficient P was calculated from the equation $P=(1/I_0) (dI/dt)_0 (r/2)$, where $I_0$ is the fluorescent intensity of the image outside of the tube at time zero, $(dI/dt)_0$ is the initial rate of increase in intensity as BSA diffuses out of the tube, and r is the tube radius. Image intensities were measured using Leica confocal software, with $(dI/dt)_0$ estimated by plotting the image intensity outside of the tube versus time over the first 4 minutes of diffusion and calculating the slope (LCS Lite, Leica Microsystems, Mannheim/Wetzlar, Germany).

Figure 6:
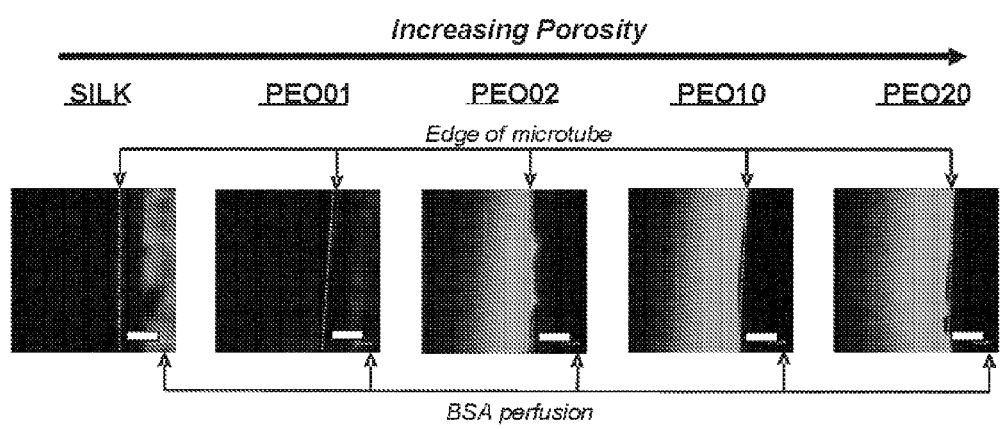
FIG. 6. Permeability of silk microtubes as a function of tube porosity. Silk microtubes embedded in a collagen gel were perfused with labeled BSA, and fluorescent confocal microscopy images are shown after 10 minutes of perfusion. Edges of microtubes are shown at the right of each image with labeled BSA diffusing out to the left of the microtube (edge of microtube given by dashed line). Labeled BSA can be seen perfusing through the middle of the 100% silk fibroin tube and is faintly visible in the PEO01 tube. Labeled protein is not visible in the middle of silk microtubes with greater percentages of PEO due to the opaqueness of the tubes. Scale bars=300 microns.

Silk microtube permeability was measured by perfusing the tubes with Alexa-Fluor-488-labeled BSA while embedded in an acellular collagen gel. Using fluorescent confocal microscopy, time-lapse images were taken every minute over a 20-minute perfusion time for microtubes manufactured with different silk fibroin/PEO ratios. These images indicated that there is an increase in microtube permeability as the pore size distribution in the microtubes is increased, due to the use of higher concentrations of PEO in the microtube production (FIG. 6). Silk (100% fibroin) microtubes exhibited a strong barrier function, allowing little to no perfusion of BSA through the tubes over the course of the 20-minute perfusion time. Labeled BSA was clearly visible perfusing through the silk microtube due to the optical clarity of the microtube. Microtubes with increasing PEO concentrations were more opaque, eliminating this visual identification of labeled BSA within the silk microtube. These fibroin/PEO microtubes, with their increased pore sizes, demonstrated diffusion of the labeled BSA from the microtubes and into the collagen gel. The apparent permeability coefficient of these porous tubes were estimated to be $1.1 \times 10^{-5} \pm 7.6 \times 10^{-6}$, $7.3 \times 10^{-4} \pm 1.5 \times 10^{-4}$ cm/s, $7.3 \times 10^{-4} \pm 0.55 \times 10^{-4}$ cm/s, and $9.4 \times 10^{-4} \pm 1.9 \times 10^{-4}$ cm/s for 99/1, 98/2, 90/10, and 80/20 wt % silk fibroin/PEO microtubes (n=3), respectively. The low tubes with small pore sizes (99/1 wt % silk fibroin/PEO) had a permeability coefficient that was an order of magnitude lower than those of the tubes with large pore sizes and was also comparable to values achieved using endothelial cell-lined microvascular tubes embedded in collagen (Chrobak K M, et al., 2006, Microvasc Res May; 71(3):185-196). In these acellular experiments, after twenty minutes of perfusion, the collagen gel was near saturation for the 90/10 and 80/20 wt % silk fibroin/PEO microtubes, consistent with their larger sized pore distribution.

Example 6. Characterization of Silk Fibroin and Silk Fibroin/PEO Microtubes—Cellular Permeability Cell Culture Human umbilical vein endothelial cells (HUVECs) were cultured according to company protocols. Briefly, HUVECs (Cambrex, Walkersville, Md.) were grown in optimized growth media (EGM-2) consisting of Endothelial Basal Medium-2 supplemented with EGM-2 Bullet kit (Cambrex), along with 100 U/mL penicillin, 1000 U/mL streptomycin, and 0.2% fungizone antimycotic (GIBCO, Carlsbad, Calif.). Cells were cultured at 37° C., 5% $CO_2$/95% air, and 95% relative humidity. Cell culture medium was replenished twice per week, and cells were passaged at approximately 80% confluence using Trypsin-EDTA (0.25% trypsin with 1 mM EDTA·4Na) and frozen in cryogenic media consisting of growth medium supplemented with 8% (v/v) dimethyl sulfoxide (DMSO).

Generation of Green Fluorescent Protein (GFP) Expressing HUVECs

A GFP-expressing line of HUVECs was generated using a previously described lentivirus system (Rubinson D A, et al., 2003, Nat Genet 33(3):401-406). HUVECs were transduced at MOI 1 (multiplicity of infection), with five milliliters of virus-containing supernatant (100,000 virus particles/mL) added to $5 \times 10^5$ HUVECs. An additional 5 mL of EGM-2 media was added in the flask along with protamine sulfate (6□g/ml) to enhance the infection. The cells were incubated for 3 hours with the lentivirus, then washed twice with PBS before adding EGM-2 media. The efficiency of GFP transduction was evaluated through fluorescence microscopy and fluorescence-activated cell sorting (FACS) analysis (BD, Franklin Lakes, N.J.). Upon generation of stable GFP-expressing HUVECs (GFP-HUVECs), cells were cultured according to standard HUVEC protocol as described above.

Perfusion of Silk Microtubes with GFP-Labeled Endothelial Cells

To assess cellular migration through the silk microtubes, they were perfused with GFP-HUVECs. The silk microtubes were maintained within an acellular collagen gel in the bioreactor set-up as described above. GFP-HUVECs were maintained and harvested according to the above protocols to a concentration of $5 \times 10^6$ cells/mL. This suspension of GFP-HUVECs was then perfused using a remote push-pull syringe pump (Harvard Apparatus, Holliston, Mass.), programmed to flow at a rate of 4 μL/min into the bioreactor for 2.5 hours before reversing perfusion and flowing at the same rate in the opposite direction. This perfusion kept the GFP-HUVECs flowing within the microtube in a back-and-forth manner, over the course of three days. Permeability of the silk microtubes to GFP-HUVECs was assessed using confocal microscopy.

Figure 8:
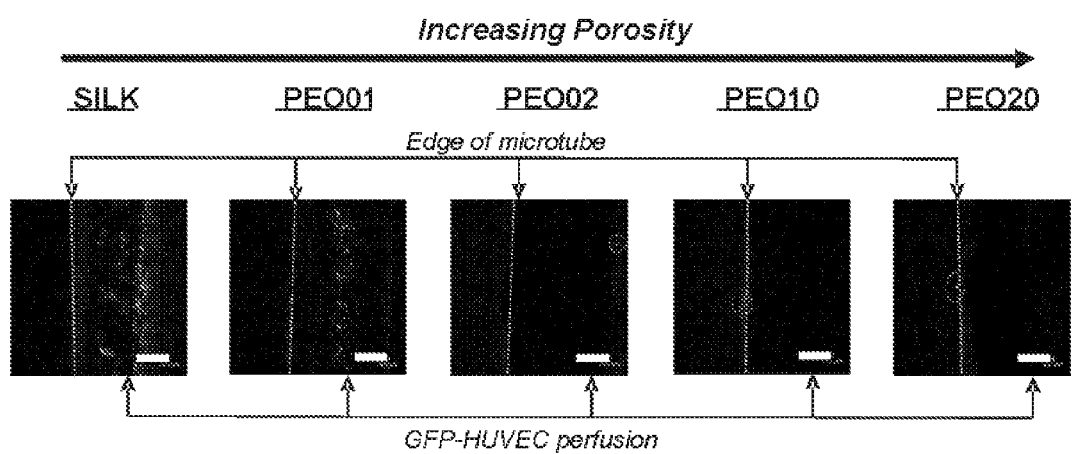
FIG. 8. Perfusion of GFP-transduced human umbilical vein endothelial cells (HUVECs). Silk microtubes embedded in a collagen gel were perfused with green fluorescent protein (GFP) transduced HUVECs. GFP-HUVECs were perfused back and forth at a rate of 4 µL/min through the silk microtubes using a syringe pump, and fluorescent confocal microscopy images are shown after 3 days of perfusion. Sections of the microtubes are shown at the right of each image with GFP-HUVECs present in the channel of the microtube (edge of microtube given by dashed line). These cells are visible in the 100% silk fibroin and PEO01 tubes, but their presence in the microtubes with greater percentages of PEO is obscured due to the opaqueness of the tubes. The silk microtubes were a significant barrier to cell migration. At low porosity, GFP-HUVEC migration was completely blocked; at higher porosities (PEO10 and PEO20) cell migration was limited to a few cells (outlined by dashed ovals) over the entire microtube. Scale bars=300 microns.

Silk microtubes of all pore size distributions limited migration of HUVECs over the course of a three day perfusion. Either no cells, or only a few GFP-transduced HUVECs per microtube, were detected outside in the surrounding collagen gel. (FIG. 8), demonstrating potential for pre-endothelialization. A high concentration ($5 \times 10^6$ cells/mL) of GFP-HUVECs was used in order to easily detect perfusion and migration of the cells through the microtubes, with cells imaged through the use of fluorescent confocal microscopy. Images throughout the microtube were taken after three hours and three days of perfusion. As in the protein diffusion experiments, GFP-HUVECs were only visible in the lumen of the tubes at the highest concentration of silk (100% fibroin and 99/1% fibroin/PEO). These tubes exhibited the strongest barrier function for endothelial cells, as none were found to migrate into the collagen gel. Microtubes of higher permeability, however, demonstrated limited cell migration into the collagen gel, typically at a rate of a few cells per tube over the three day perfusion. Taken together with the protein diffusion data, the microtubes demonstrate the ability to selectively allow protein diffusion through the microvascular graft, while largely preventing any cell migration. This ability to reduce cellular migration offers the opportunity for these microtubes to be pre-endothelialized before implantation as a microvascular graft, a technique often considered to be critical for the prevention of thrombosis in tissue-engineered vascular grafts (Mitchell S L, and Niklason L E, 2003, Cardiovasc Pathol 12(2):59-64).

Silk microtubes were assessed for enzymatic degradation over time using a protocol described previously (Horan R L, et al., 2005, Biomaterials 26(17):3385-3393). Briefly, silk microtubes (1 cm in length, N=3 per group and time point) were incubated in 1 mL of 1.0 mg/mL Protease XIV (5.3 units/mg, Sigma-Aldrich, St. Louis, Mo.) in PBS or in PBS as a negative control at 37° C. for a period of ten days. Solutions were changed daily and samples were taken every 3-4 days. Samples were washed once with PBS before drying overnight in a laminar flow hood. Samples were weighed and compared to their initial weight.

Figure 7:
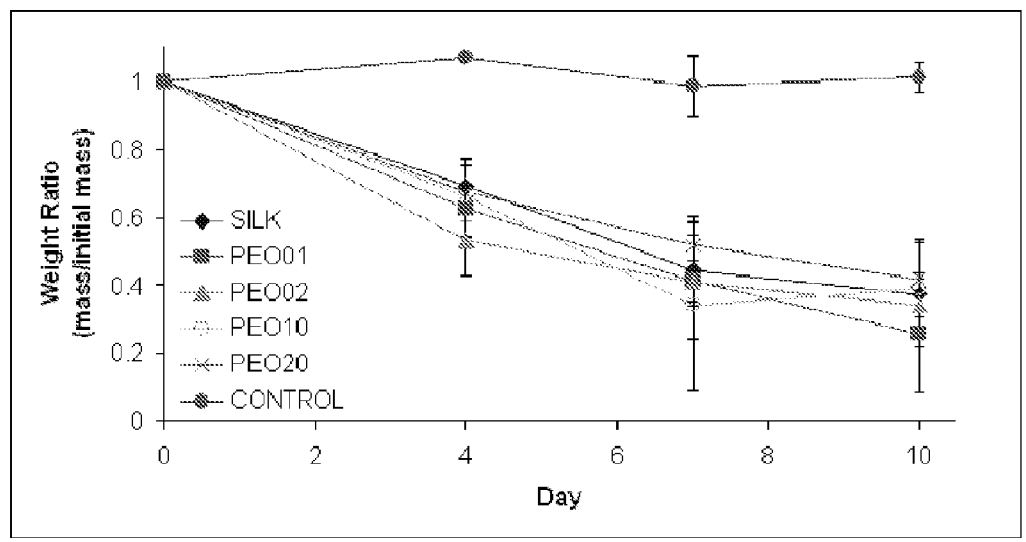
FIG. 7. Enzymatic degradation of silk microtubes. Silk microtubes were degraded over time in 1.0 mg/mL protease or in PBS (control). Data is reported as a weight ratio of microtube mass on day of sampling divided by initial mass of microtube.

Example 7. Characterization of Silk Fibroin and Silk Fibroin/PEO Microtubes—Enzymatic Degradation Silk microtubes were subjected to an in vitro proteolytic digest over the course of ten days to track degradation over time. Protease (Protease XIV) was chosen based on previously reported results on the degradation of silk fibroin fibers (Horan R L, et al., 2005, Biomaterials 26(17):3385-3393). For silk fibroin microtubes, degradation was observed in all silk samples incubated in the protease solution, demonstrating a general linear degradation rate in terms of weight ratio based on the sample mass at each time point divided by initial microtube mass (FIG. 7). At each progressive time point, silk microtubes were considerably more brittle, demonstrating a loss of mechanical integrity as they degraded by gross observation. Control samples incubated in PBS did not exhibit any mass loss and were observed to be typical in terms of microtube integrity at all time points. Interestingly, silk microtube degradation was not dependent on microtube permeability as all microtubes displayed a similar linear trend. This may be due to the methanol treatment used in all formulations of silk tubes, creating the β-sheet structure discussed previously in all tubes, or the relatively small tube sizes used (~1 cm length) which may mask the effects of porosity.

Example 8. Silk Microtubes with Different Diameters

Figure 9:
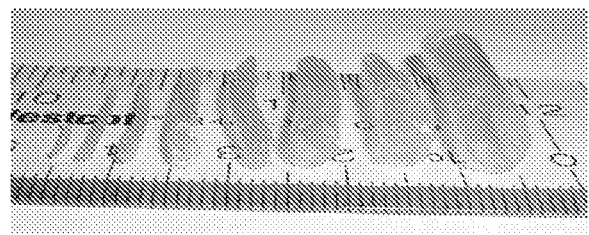
FIG. 9. Silk microtubes at a range of diameters. Stainless steel wire and rods were used to generate silk tubes with approximate inner diameters of (from left to right): 127 µm, 500 µm, 1 mm, 2 mm, 3.2 mm, 4 mm, 5 mm, and 6 mm. This demonstrates that these silk microtubes can be easily generated for any size microvascular graft (<6 mm diameter).

In order to demonstrate the general applicability of this technique towards microvascular grafting, tubes were manufactured in a range from 100 μm ID to 6 mm ID, the generally reported maximum diameter to be considered a microvascular graft. The dipping technique allows tubes to be formed with different diameters quickly and easily, as opposed to other silk-based techniques such as electrospinning, which requires optimization of multiple processing steps (e.g. mandrel selection, voltages, etc.) (Soffer L, et al., J Biomater Sci Submitted). Tubes of approximately 127 μm, 500 μm, 1 mm, 2 mm, 3.2 mm, 4 mm, 5 mm, and 6 mm ID were successfully generated using the dipping technique (FIG. 9), although those larger than 2 mm ID were occasionally subject to cracking as the silk dried around the stainless steel wire or rods after methanol treatment.

An important feature of the process is the all aqueous solution used during vessel formation. This allows the incorporation of labile molecules or therapeutics into the coatings with retention of bioactivity, as has been previously shown for BMP-2 (Li C, et al., 2006, Biomaterials 27(16): 3115-3124). It has been previously shown that the methanol used in the process, to induce beta sheet formation and thus stability in water, can be replaced with a nitrogen gas drying step (Wang X, et al., 2005, Langmuir 21(24):11335-11341), a useful option to functionalize these new microvessels with therapeutics. Notably, this can all be done in the context of matching silk tube design specifications to specific applications, creating a good balance between porosity, transport properties, mechanical properties, and tube size. For example, a patient in need of a larger diameter (4-5 mm ID) graft can be manufactured a silk tube of this exact inner diameter, with low porosity (as transport is not critical at that size), and definable wall thickness (controlled by number of dips in silk fibroin) based on some measure of the required mechanical load on the graft (e.g. blood pressure). This kind of versatility positions these silk microtubes as a powerful new method of creating microvascular grafts for applications in medicine and tissue engineering.

The ability to form small tubes (0.1 to 6.0 mm ID) with controllable pore sizes with silk fibroin aqueous solution, the superior mechanical properties, slow biodegradation and the biocompatibility of this protein provides a novel option for microvascular grafts. These properties can be tailored through the addition of various concentrations of polyethylene oxide (PEO) or other biocompatible polymer to silk fibroin before forming the silk microtubes through a simple dipping technique, and leaching out the PEO or other polymer to generate the porous silk microtubes. Recent reports have suggested the need for porous scaffolds for vascular tissue engineering applications (Sarkar S, et al., 2006, Biomaterials 27(27):4775-4782), and these porous silk microtubes can address this need. The porous silk microtubes were characterized in terms of pore size, burst pressure, protein diffusion, enzymatic degradation, and cell migration. Higher concentrations of silk fibroin (100/0, 99/1 wt % silk fibroin/PEO) produced microtubes that exhibited the lowest pore sizes, highest burst pressures, and strongest barrier function for both protein diffusion and cell migration. Greater concentrations of PEO (90/10, 80/20 wt % silk fibroin/PEO), however, produced the opposite effect as these microtubes had larger pore sizes, lower burst pressures, higher rates of protein diffusion, and occasional cell migration. In between these two extremes, silk tubes of 98/2 wt % silk fibroin/PEO had burst pressures on par with those of 100% silk fibroin microtubes, and also demonstrated a permeability to small proteins while limiting endothelial cell migration. This type of microtube may represent a useful next step for microvascular grafts since it is capable of withstanding physiological pressures, while also allowing for protein diffusion and endothelialization.

This ability to control properties of the microtubes, combined with their relative ease of manufacture compared to other techniques provides an attractive option for vascular applications. As a microvascular graft material, these microtubes offer the benefit of being capable of being functionalized via the facile attachment of RGD-peptides and other peptides or proteins as described in previous work (Sofia S, et al., 2001 J Biomed Mater Res 54(1):139-148). Carbodiimide coupling chemistry is useful in this regard, although any coupling approach known to those skilled in the art can be used. This chemical modification of the silk would allow for control over the luminal endothelialization of the microtubes, a factor critical for improved patency rates in in vivo implantation studies. Overall, these silk microtubes represent a simple method of controlling critical microvascular properties, offering opportunities for advancement over existing materials in tissue engineering for both in vivo and in vitro applications.

The invention claimed is:

1. A tubular composition in which a silk fibroin material forms a wall that defines an inner lumen having a diameter of less than 6 mm, and has a structure, including pore size, wherein the tubular composition achieves a burst strength of at least 1680 mm Hg, and wherein said wall has an apparent permeability coefficient of $7.3 \times 10^{-4} +/- 1.5 \times 10^{-4}$ cm/s or lower.

2. The composition of claim 1, wherein the silk fibroin material comprises a plurality of layers of silk fibroin.

3. The composition of claim 1, wherein the inner lumen diameter is 0.1 mm to 5.9 mm.

4. The composition of claim 1, wherein said silk fibroin material is predominantly in a β-sheet conformation.

5. The composition of claim 1, further comprising: at least one endothelial cell within the lumen and associated with the wall of the tubular composition.

6. The composition of claim 1, wherein the silk fibroin material comprises a functional moiety coupled to silk fibroin.

7. The composition of claim 6, wherein said functional moiety comprises an RGD peptide.

8. The composition of claim 1, further comprising a bioactive material associated with the silk fibroin material.

9. The composition of claim 8, wherein said bioactive material is selected from the group consisting of a cell, a peptide, a polypeptide and/or a therapeutic agent.

10. The tubular composition of claim 1, wherein the silk fibroin material comprises silk fibroin and polyethylene oxide.

11. The composition of claim 10, wherein the silk fibroin material comprises a plurality of layers.

12. The composition, of claim 1, wherein the tubular composition is self-supporting in that it does not rely upon another material for its physical support or tubular shape.

13. The composition, of claim 12, wherein the tubular composition is not a tubular construct in which a framework or support made of another material is coated with silk.

14. The composition of claim 12, wherein the tubular composition is not a stent or other structure that carries a coating comprising or consisting of silk on inner or outer surfaces or both.

15. The tubular composition of claim 1, wherein the burst strength is at least 2460 mm Hg.

16. The tubular composition of claim 1, wherein the burst strength is at least 2470 mm Hg.

17. The tubular composition of claim 1, wherein the burst strength is at least 2780 mm Hg.

18. A method of making the tubular composition of claim 1, the method comprising steps of:
   (a) providing an aqueous preparation of silk fibroin;
   (b) contacting a rod of a selected diameter with the aqueous preparation of silk fibroin to coat the rod in silk fibroin;
   (c) drying the silk fibroin so that a silk fibroin material is formed as a coating on the rod; and
   (d) removing the silk fibroin material from the rod, the silk fibroin material being in a tubular shape,
   so that the tubular composition of claim 1 is prepared with a permeability coefficient of $7.2 \times 10^{-4} +/- 1.5 \times 10^{-4}$ cm/s or lower.

19. The method of claim 18, wherein steps (b)-(c) are repeated at least once, so that the silk fibroin material comprises at least two layers of silk fibroin.

20. The method of claim 18, further comprising a step of contacting the rod with methanol after step (b).

21. The method of claim 18, wherein the aqueous preparation of silk fibroin comprises polyethylene oxide, so that the silk fibroin material comprises silk fibroin and polyethylene oxide.

22. A method of repairing or replacing a blood vessel in a mammal in need thereof, the method comprising implanting in said mammal the tubular composition of claim 1, wherein said implanting repairs or replaces the blood vessel in said mammal.

23. A kit comprising the tubular composition of claim 1, and packaging materials therefor.

* * * * *

UNITED STATES PATENT AND TRADEMARK OFFICE
CERTIFICATE OF CORRECTION

PATENT NO. : 9,808,557 B2  
APPLICATION NO. : 12/672521  
DATED : November 7, 2017  
INVENTOR(S) : Michael L. Lovett et al.

Page 1 of 1

It is certified that error appears in the above-identified patent and that said Letters Patent is hereby corrected as shown below:

On the Title Page

Item (73) ("Assignees") delete "Massachussets" and insert --Massachusetts--.

Signed and Sealed this  
Twenty-sixth Day of December, 2017

Joseph Matal  
*Performing the Functions and Duties of the*  
*Under Secretary of Commerce for Intellectual Property and*  
*Director of the United States Patent and Trademark Office*